United States Patent
Lal et al.

(10) Patent No.: US 10,431,330 B2
(45) Date of Patent: Oct. 1, 2019

(54) METHOD AND SYSTEM TO PROVIDE PATIENT INFORMATION AND FACILITATE CARE OF A PATIENT

(71) Applicant: Children's Hospital & Research Center at Oakland, Oakland, CA (US)

(72) Inventors: Ashutosh Lal, Moraga, CA (US); Shanda M. Robertson, Berkeley, CA (US); Elliott P. Vichinsky, Oakland, CA (US)

(73) Assignee: CHILDREN'S HOSPITAL & RESEARCH CENTER AT OAKLAND, Oakland, CA (US)

( * ) Notice: Subject to any disclaimer, the term of this patent is extended or adjusted under 35 U.S.C. 154(b) by 171 days.

(21) Appl. No.: 14/161,526

(22) Filed: Jan. 22, 2014

(65) Prior Publication Data
US 2015/0205919 A1 Jul. 23, 2015

(51) Int. Cl.
*G16H 10/60* (2018.01)
*G06F 19/00* (2018.01)

(52) U.S. Cl.
CPC ............. *G16H 10/60* (2018.01); *G06F 19/00* (2013.01)

(58) Field of Classification Search
CPC ........ G06Q 50/22; G06Q 50/24; G16H 10/60; G06F 19/00
See application file for complete search history.

(56) References Cited

U.S. PATENT DOCUMENTS

| | | | |
|---|---|---|---|
| 6,182,221 B1 * | 1/2001 | Hsu .................. | G07C 9/00087 380/285 |
| 2001/0048359 A1 * | 12/2001 | Yamane ................. | G06F 21/32 340/5.53 |
| 2006/0085226 A1 * | 4/2006 | Kamber ............... | G06F 19/323 705/2 |
| 2006/0229918 A1 * | 10/2006 | Fotsch .................. | G06F 19/322 705/3 |
| 2006/0259331 A1 * | 11/2006 | Lurtz .................... | G06Q 50/24 705/3 |
| 2008/0028230 A1 * | 1/2008 | Shatford .............. | H04L 9/3231 713/186 |
| 2009/0019552 A1 * | 1/2009 | McLaughlin ........ | G06F 19/322 726/27 |
| 2009/0063190 A1 * | 3/2009 | Firozvi ................ | G06F 19/324 705/3 |

(Continued)

*Primary Examiner* — Joy Chng
*Assistant Examiner* — Evangeline Barr
(74) *Attorney, Agent, or Firm* — Perkins Coie LLP

(57) ABSTRACT

A computer system for facilitating care of a patient with a rare, complex, or chronic medical condition is provided. The system may include a server and a patient data module programmed to receive patient medical records pertaining to a patient, process the patient medical records to extract patient medical data pertaining to the patient, create a patient webpage specific to the patient which includes the patient medical data, and store the patient webpage. The system may also include a patient identification card provided to the patient which has an internet URL corresponding to the patient webpage encoded within a machine readable code. The patient data module may be programmed to receive, from a computer, a request to view the internet URL and transmit the patient webpage to the computer.

19 Claims, 11 Drawing Sheets

(56) References Cited

U.S. PATENT DOCUMENTS

| | | | | |
|---|---|---|---|---|
| 2010/0082371 A1* | 4/2010 | Kamp | ............... | G06Q 10/06 705/3 |
| 2011/0137804 A1* | 6/2011 | Peterson | ............ | G06Q 20/085 705/77 |
| 2013/0290013 A1* | 10/2013 | Forrester | ............. | G06F 19/323 705/2 |

* cited by examiner

METHOD AND SYSTEM TO PROVIDE PATIENT INFORMATION AND FACILITATE CARE OF A PATIENT

BACKGROUND INFORMATION

Field of the Disclosure

The present invention relates to care of a patient. In particular, examples of the present invention relate to a system for providing patient information to medical care staff to facilitate more accurate care of patients.

Background

Many patients have rare or complex medical conditions which require a specialized level of care, are engaged in ongoing care for a medical condition, etc. These patients are typically treated by a primary doctor or a team of medical professionals. In some situations, these patients may be treated by medical professionals who are not their usual care provider. This may be when the patient is out of town or when the patient experiences a medical emergency. In these situations, the medical care provider may be unable to provide the same quality of care to the patient that would be received from their primary care doctor.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
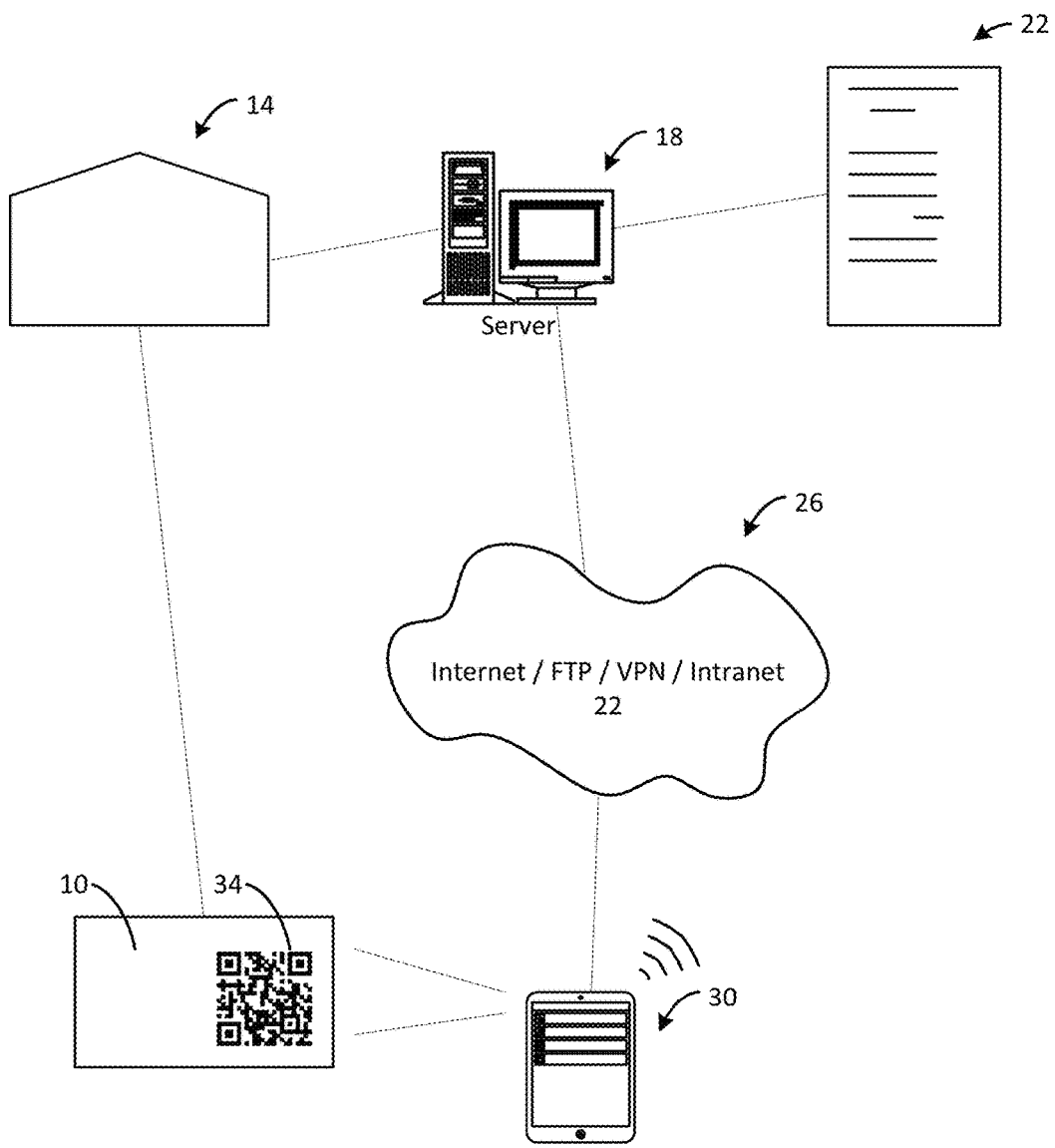
FIG. 1 is a schematic illustrating a computer system in context of a patient identification card.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The disclosure particularly describes how to provide current information regarding a patient to treating medical persons and to facilitate proper care of the patient. Particularly, the present disclosure describes how a computer system may be used to provide detailed care information for a patient to medical professionals caring for the patient to assist these persons in properly caring for the patient. Also, those skilled in the art will understand that the examples below may be adapted to information related to animals, including pets, livestock, endangered species, test animals, and other non-human applications.

Many patients have ongoing medical problems or conditions which necessitate continuing treatment. These medical conditions are typically less common and many doctors will be unfamiliar with these conditions are they are not specialized in the particular area of medicine. For example, many blood diseases, cancers, etc. require that a patient receive specialized care.

Patients with rare, complex, or chronic diseases often have extensive medical histories that need to be made available to doctors (used herein to refer to emergency medical providers, doctors, etc.) to facilitate treatment of the patient. Immediate accessibility of records from the patient's healthcare provider is important when such a patient comes to an emergency room or other medical facility to receive treatment. Such patients have complicated treatment plans and complex conditions which require a more thorough knowledge of the patient and the patient's history to treat the patient. A doctor who is not the primary care provider for the patient needs access to the patient's care history so that any treatment is consistent with the course of action decided by the primary care provider.

Where a patient with a rare, complex, or chronic condition requires treatment, the treatment should often be based on their past treatment so that the new treatment is complementary to the past treatment. Additionally, new treatment of a patient should not cause an adverse reaction to previously administered drugs or therapy. Critically ill patients and patients with rare or complex diseased may have frequent changes in medication and treatment. As such, a doctor should not simply treat with any of available medications, but should continue with the medication currently being used. Where a patient has a rare condition, a general practice doctor or emergency care doctor may simply not have enough information about a condition to effectively treat the patient. A specialist doctor may have adequate knowledge about a particular condition, but not have sufficient knowledge about the particular patient to effectively treat the patient.

Treatment of a patient should begin at a level which is effective for the patient. For example, patients with chronic pain frequently require a higher dose of pain medication to treat the pain than another patient with a similar but non-chronic pain. Without patient history, however, a treating doctor will frequently begin with a minimum dose of medication. The doctor may gradually increase the dose until it becomes effective, but this results in an extended time period where the patient is not being treated effectively.

Static patient identification tags, such as bracelets, may identify that a patient has a particular condition, but do not provide additional information. This is often sufficient for conditions such as allergies, but such an identification tag does not provide sufficient information about a complex condition to facilitate ongoing treatment as the identification tag is not up to date and provides a low amount and quality of information. For rare or complex conditions, incomplete listings of diseases or conditions and information which are not up to date would often result in the wrong treatment for a patient's condition.

A computer system is utilized to provide thorough and up to date information about a patient to a doctor who is not familiar with the patient and who may not have access to the patient's medical records. The computer system may upload/update medical records to a database and may link the database to a webpage. The computer system may process the medical records to remove sensitive information or to extract desired information. The computer system may create a patient webpage containing information from the patient's medical records. The webpage may be a plain html webpage that any internet enabled phone or computer can read. The computer system may create a patient identification card. The patient identification card may be presented to the patient and the patient can carry the card with them. The patient identification card may have an internet URL (Uniform Resource Locator) and a machine readable code such as a QR code. The URL and machine readable code may correspond to the webpage which contains information from the patient's medical records. The QR code may be scanned by a computer including a portable electronic device, smart phone, or tablet computer, and scanning the QR code may direct the internet browser of the electronic device to load and view the patient webpage. Thus, scanning the QR code or entering the URL will bring up the personalized webpage for the patient and show up to date information from the patient's medical records.

A patient identification card may contain basic information such as the patient's name, date of birth, diagnosis (i.e. medical conditions), allergies, and healthcare provider names and phone numbers in addition to a QR (quick response) barcode. The QR code may be created such that it may be scanned with any QR code reader application. These applications are free and available for any smartphone. This will allow an emergency healthcare provider to access a personalized web site containing the patient's relevant medical information. The doctor may obtain clinical summaries, currently prescribed medications and dosages, recent transfusions and transfusion plan, red blood cell antibody and antigen data, patient encounters, recent laboratory and imaging results, physician contact information, and more.

The computer system may be dynamic and the patient information in a database and the patient webpage may be continuously updated as the patient is treated. The system may thus provide a doctor with up to date treatment information. The patient webpage is platform independent and accessible from any mobile device or computer which is internet enabled. Any QR code scanning application on a phone, laptop, desktop, etc. can access it and a computer without a QR code scanning application may manually enter a URL to retrieve the patient webpage.

The computer system allows a doctor to provide proper care to a patient instead of just stabilizing the patient and admitting them to a hospital or transferring them to another hospital. The computer system allows the hospital or doctor to provide the best treatment to the patient.

The computer system may provide information to doctors to describe the patient's condition, current treatment, medications, etc. to allow the doctor to provide care to the patient. Additionally, many medical conditions may alter the care which must be provided to a patient for other medical problems. For example, it may be detrimental to give a patient a particular drug due to another drug that the patient is taking or due to a medical condition affecting the patient.

The present system may be used to provide up to date medical information to a doctor for a patient. The information may guide the doctor in treating the patient; either for an ongoing condition or for a new medical condition. The medical information may be provided electronically to the doctor, and a thorough medical history may be provided rather than simply identifying a medical condition. The medical information may include treatment guidelines for a patient's medical condition, and may include treatment protocols which work for the particular patient.

Referring to FIG. 1, a system may include one or more patient identification cards 10. The patient identification card 10 may be issued by a hospital 14 or another facility. Typically, the patient identification card 10 is associated with a facility which is primarily responsible for providing medical care to a patient associated with the patient identification card 10. The system may also include a server 18 or other computer associated with the medical facility 14. The server 18 may facilitate the collection and presentation of information regarding the patient. The server 18 may prepare a webpage 22 with information regarding the patient and associated with the patient information card 10. The server 18 may communicate with other computers via the internet 26 or other communication systems.

The computer system may also include other computing devices. Particularly, the system may include a computer 30 associated with a medical professional who is providing care to the patient. For clarity in discussing the system, the term "doctor" may be used herein to represent a variety of medical professionals who may be providing care to a patient. The term doctor may be used to describe emergency medical technicians, nurses, physicians, etc. A doctor may use a computer 30 to receive information regarding a patient and use the patient information to provide better care to the patient.

The computer 30 may be a portable computing device 30 such as a smart phone or tablet computer. The computer 30 may communicate with other computers or devices which may include the server 18. The computer 30 may communicate via the internet 26. The computer 30 may be used by a doctor to view a webpage 22 associated with the patient and with the patient identification card 10. The computer 30 may be used to scan information on the patient identification card 10 to retrieve information from the website 22. The patient identification card 10 may include a QR code 34 or other machine readable code. The computer 30 may read the QR code and automatically load the webpage 22 to retrieve patient information.

Various different types of computers 30 may be used. A tablet computer 30 may be used by hospital staff, transport staff while transporting a patient between or to a care facility, or by emergency responders. A smart phone 30 may be used by a doctor who encounters a person needing medical assistance. A desktop computer 30 may be used at a hospital or other facility in providing care to patients.

The server 18 may store patient data, care information, patient care protocols, or the like and may often be located at a care facility such as a hospital. The server 18 may be connected to the internet via a modem, router, or the like. The server 18 may process patient data to extract desired information from hospital records and prepare a webpage 22 which contains desired information related to the patient, patient conditions, and patient care.

The various types of computers 30 may be connected to the internet via a wired or wireless router when such a connection is available, such as when in proximity to a care facility. The computers 30 may also be connected to the internet via a cellular network to provide communications when a computer 30 is not in communication range of a wireless router or the like.

The software, hardware, and associated components of a computer system may be programmed and configured to implement one or more embodiments described herein. Doctors may communicate with a care facility server 18 via a computer 30 and a network connection or internet connection 26 to receive patient care information from the server 18. Particularly, the computer 30 may retrieve detailed and up to date patient information and patient care information which is specific to the treatment history and condition of the individual patient.

To participate in the patient identification card system, patients will be contacted and presented information about the identification card program as they come to a hospital or clinic. Patients who desire an identification card will sign a consent form and enroll to receive an identification card. Patients who have been seen at a hospital or clinic in a previous time period, such as the past 6 months, may be mailed a sample patient identification card and report (patient webpage data) along with a consent/enrollment form. If the patient desires to participate in the program, they may sign and return the consent form. The consent form may include an agreement for the patient to notify their primary care doctor/clinic if they lose their patient identification card. This may facilitate the safeguarding of the patient's medical information.

A patient identification code is generated for patients who have enrolled to receive a patient identification card. The patient identification code may be randomly generated so that the identity of the patient cannot be determined from the patient identification code and so that a patient identification code cannot be determined from the identity of a patient. An entry in a patient database may be created which is associated with the patient identification code. Additionally, a webpage may be created which is associated with the patient identification code. The patient identification code may be a portion of the webpage URL. A QR code may be generated which points to the patient's webpage on the web server. An example patient webpage URL may be: http://www.hospitalname.org/QR/[PID].html where [PID] is replaced with the patient identification code.

Patient identification cards may be printed with a desired amount of patient identification. The patient identification card will usually be printed with the URL for the particular patient's medical information webpage as well as the QR code which will direct a computer to the webpage. The patient identification card may be printed as a wallet card. The patient identification card may be printed onto double-sided business cards.

After creation of a patient identification card, staff may verify that the card is functional by scanning the code and ensuring it retrieves the correct report. If functioning correctly, the staff may give the card to the patient. If desired, a printed copy of the patient's current medical information webpage may be provided to the patient along with the patient identification card. Staff responsible for maintaining the database and the patient webpages may regularly monitor the database and webpage directory, and may monitor the computer system to ensure that the reports are being generated.

Figure 2A:
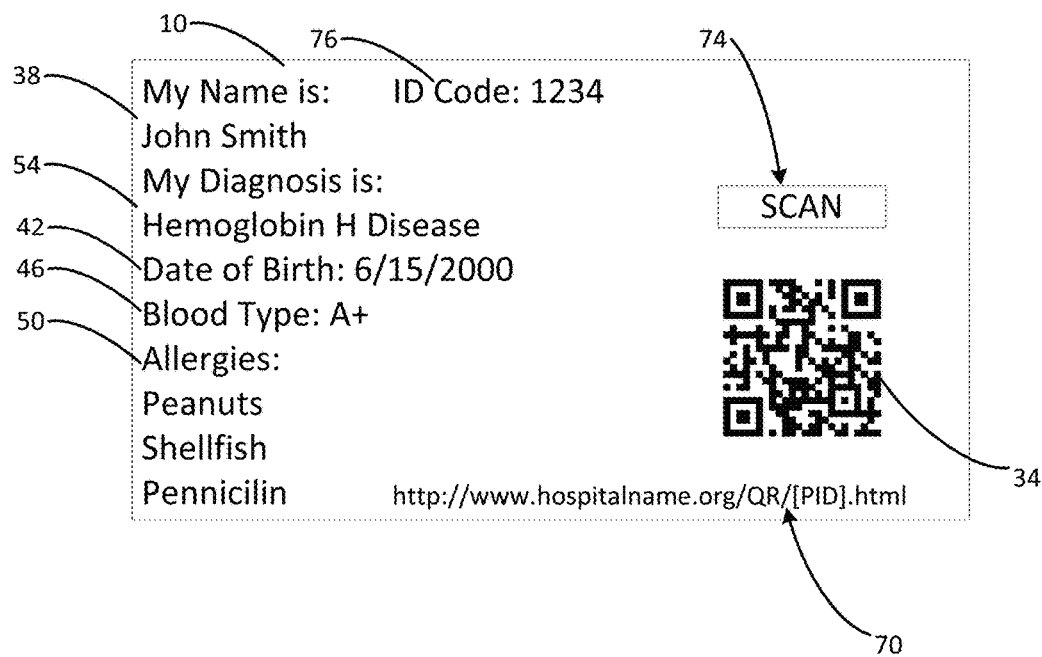
FIGS. 2A, 2B, and 2C are drawings of a patient identification card.
Figure 2B:
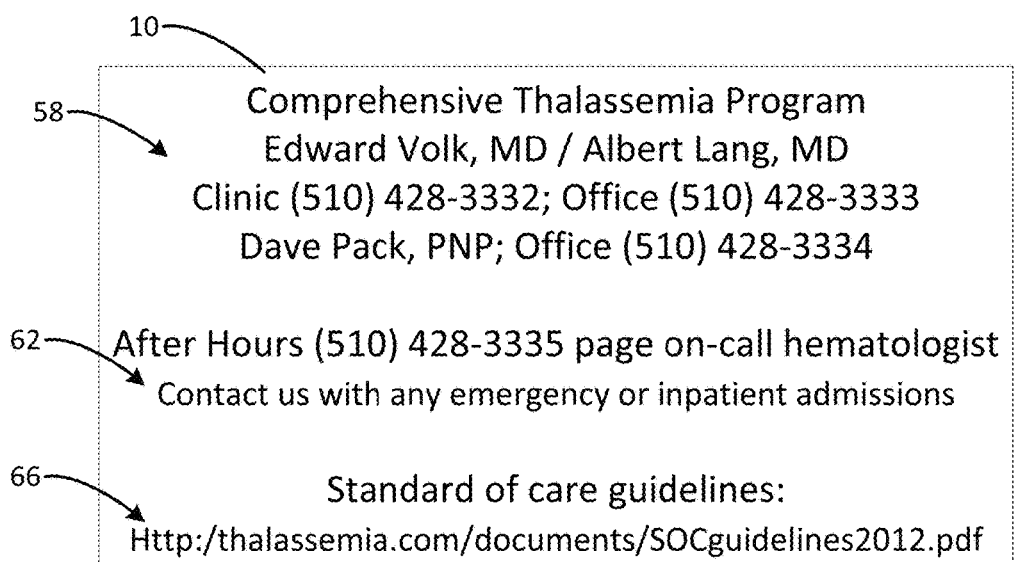

Referring to FIGS. 2A and 2B, an example patient identification card 10 is shown. FIG. 2A shows the front of the patient identification card 10 and FIG. 2B shows the back of the card. The card 10 includes some basic patient information. For example, the patient identification card 10 may include the patient's name 38, the patient's date of birth 42, blood type 46, and allergies 50. The patient identification card 10 may also include a patient diagnosis of a significant disease or medical condition 54 which afflicts the patient.

The patient identification card 10 may also include contact information 58 for the patient's primary treating doctor and hospital/clinic. The contact information 58 may include the hospital name, address, and telephone number. The contact information 58 may also include the hospital program or division which is treating the patient. The contact information 58 may also include the name of the doctor who is primarily responsible for treating the patient as well as an alternate doctor responsible for treating the patient and the telephone numbers for contacting these doctors.

The patient identification card 10 may include an instruction 62 that a doctor contact the hospital or the primary treating doctor if any emergency care or inpatient treatment is given to the patient. Such an instruction 62 will help ensure that the primary doctor is able to provide input into the treatment which is provided to the doctor who is handling the emergency treatment. Additionally, such an instruction 62 may allow the primary treating doctor to receive information about the emergency conditions, patient status, treatment and medications given to the patient and this information may be entered into the hospital server 18 and become part of the patient database and webpage 22.

The patient identification card 10 may also include an internet link 66 to standard of care guidelines. The standard of care guidelines link 66 may, via a computer web browser, direct a doctor to treatment guidelines for caring for the patient. Thus, a doctor may enter the standard of care guidelines link 66 into an internet browser on a computer (including a smart phone, tablet computer, etc.) and view a document or webpage from the hospital 14 which describes the care which should be provided to the patient based on the patient's diagnosis or medical condition 54. The standard of care guidelines may be prepared to address the medical diagnosis 54 generally and, as such, would be applicable to all patients with that diagnosis. It will be appreciated that the standard of care guidelines link 66 could also be presented as a machine readable code such as a QR code so that a doctor could simply scan the machine readable code with a computer and be directed to the standard of care document/webpage. Use of a machine readable code may eliminate a source of human error while accessing the internet URL in an emergency or while caring for the patient.

The patient identification card 10 may also include an internet URL 34 which directs a web browser on a computer to a personalized webpage 22 for the patient. The internet URL 34 may be a machine readable code such as QR code 34. The internet URL for the patient's personalized webpage 22 may also be written out in text 70. This would allow a doctor who does not have an application or the hardware to scan a machine readable code to manually enter the URL into an internet browser on a computer and retrieve the patient's personalized webpage 22.

The machine readable code 34 may be accompanied by a visible instruction 74 which directs a doctor to scan the machine readable code 34 or enter the URL 70 to view the patient's webpage 22. The instruction 74 may be a brightly colored area which grabs the attention of a doctor viewing the patient identification card 10. The instruction 74 may also provide an explanation or description of the patient webpage 22 which will be retrieved or otherwise contain text which explains to a doctor that entering the URL 70 into an internet browser or scanning the QR code 34 will retrieve a webpage with personalized medical information for the patient. The instruction 74 may indicate to the doctor that the information is pertinent to the patient's medical condition 54 and that the information is important to providing proper medical care to the patient.

The patient identification card 10 may also include a patient identification code 76. As discussed above, the patient identification code 76 may be the code assigned to the patient as part of the computer system and may identify the patient within the database and may form part of the URL of the patient webpage 22. The patient identification code 76 may be used to verify that the retrieved information pertains to the patient.

Figure 2C:
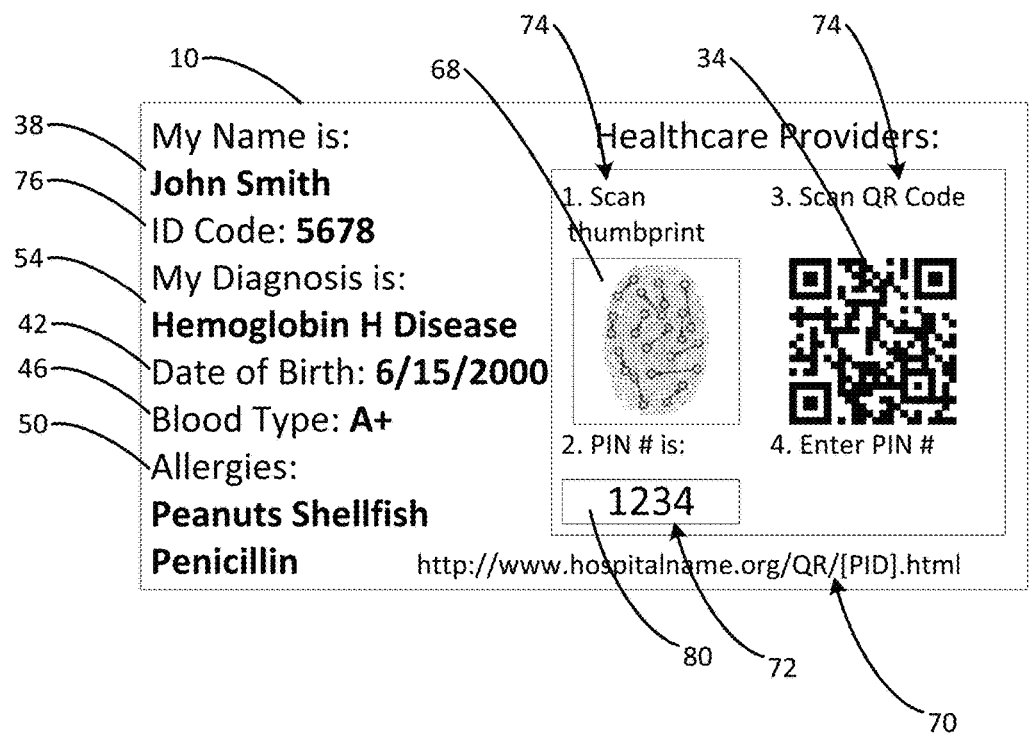

Referring to FIG. 2C, a patient identification card 10 may also include an embedded fingerprint scanner 68 as well as the necessary processor, battery source, etc. to operate the fingerprint scanner. The instructions 74 may direct a doctor to scan the patient's thumb or finger with the embedded fingerprint scanner 68. The card processor may then analyze the fingerprint/thumbprint to determine if it belongs to the patient 78. Identifying data for the patient's fingerprint/thumbprint may be stored in the card processor and the processor may compare the identifying data with the scanned fingerprint/thumbprint to determine if it is a match. If a match is found, the processor may display a PIN (Personal Identification Number) number 72 on a display screen 80. The instructions 74 may direct the doctor to scan the QR code 34 or enter the corresponding webpage URL and then enter the PIN number 72 into an authentication page for the patient webpage. Scanning the code 34 may cause the server 18 to display a simple authentication webpage on the computer 30 which has a location to receive the PIN number 72. Entry of the PIN number 72 into the authentication page may cause the server 18 to display the patient webpage 22 on the computer 30.

Figure 3:
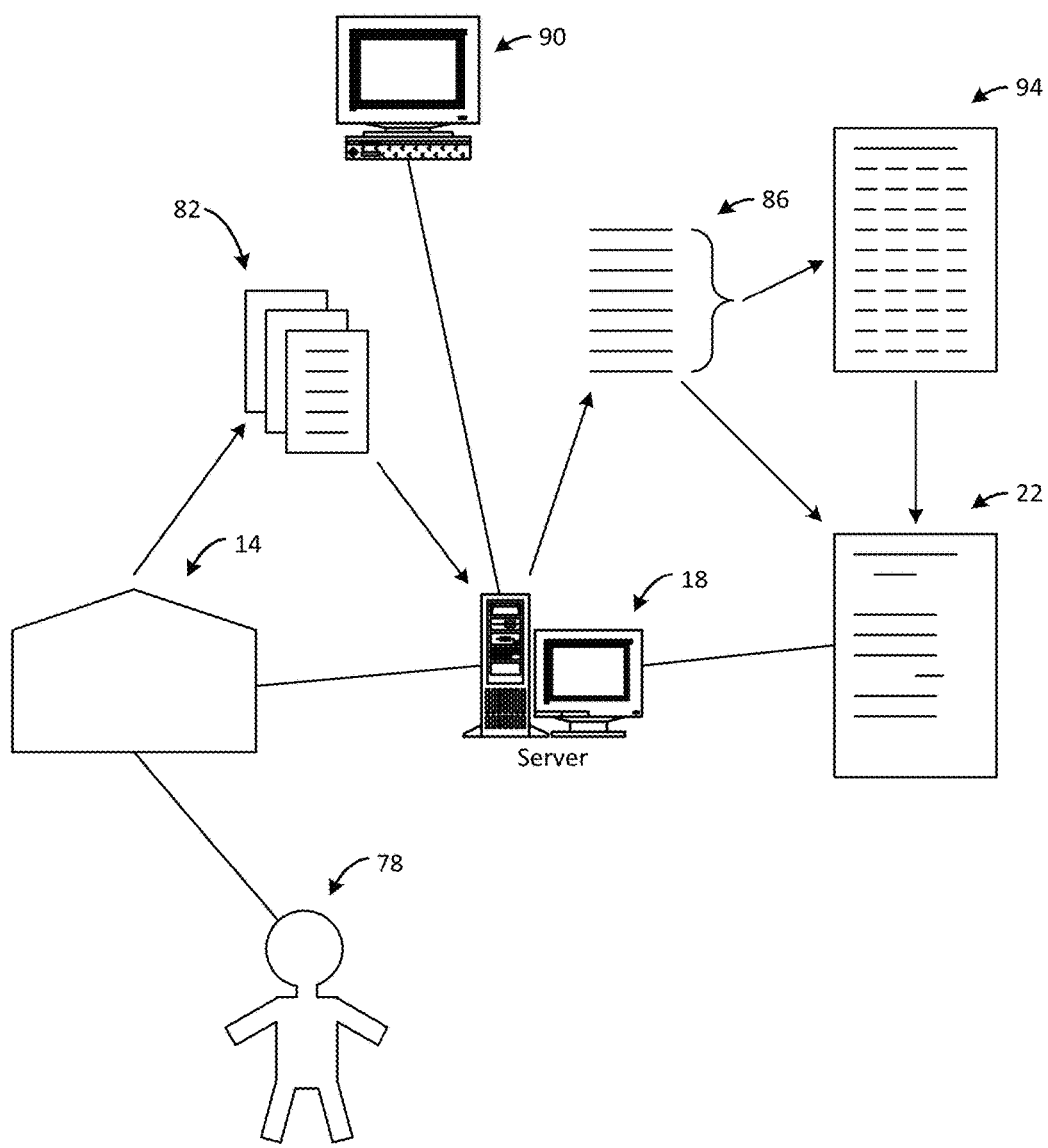
FIGS. 3 and 4 are schematics illustrating a computer system used to provide patient data and care information.

Referring now to FIG. 3, a schematic illustrating aspects of retrieving and processing information to create a patient webpage 22 is shown. Although primarily discussed in the context of one hospital 14 and one patient, the present system may be extended to encompass multiple hospitals and clinics and to encompass multiple patients. A hospital 14 is used to represent hospitals, clinics, specialty treatment facilities, etc. where medical care is provided to a patient. Similarly, where a single computer or server is shown the functionality of that device may be accomplished with multiple computer devices working together. For example, it may be desirable to have multiple servers and computers handling the functionality discussed with respect to server 18.

A patient 78 may be treated at a hospital 14. As has been discussed, the patient 78 may have a medical condition or diagnosis or treatment history which may affect future medical care provided to the patient. This becomes increasingly important where the patient is afflicted with a rare or complex disease, a chronic disease, etc. Treatment of the patient 78 may generate medical records 82. According to current practice, many of the medical records 82 are created as electronic medical records. Other medical records are entered into a computer and thus transformed into electronic medical records 82. The medical records 82 may include a variety of different types of records and may include information including patient examination and diagnosis, specific patient treatment activities, patient prescriptions, etc. The medical records 82 thus contain information about the patient's state of health, medical conditions, and treatment which would be relevant to ongoing treatment of the patient 78.

The patient medical records 82 are processed by a server 18 in the creation of a patient specific webpage 22. The server 18 may be programmed to identify data fields in the medical records 82 and extract relevant data 86 from the medical records. The server 18 may receive information from various sources within a hospital 14, such as receiving information from patient encounters, labs, medical imaging, transfusions, and pharmacies. The server 18 may also receive medical records/information from other sources. The server 18 may be connected to other computers 90 such as a hospital computer. The server 18 may thus receive information which is manually entered by staff including medical history, patient vitals and biometrics, and clinical summaries.

The server 18 may also receive medical records 82 from outside sources such as receiving immunization records. As discussed, the server 18 may be connected to multiple hospitals and care facilities and may receive medical records 82 from these institutions. The server 18 may process the medical records 82 to extract the data 86 or otherwise prepare the data contained within the medical records 82 for presentation in a patient webpage 22. For example, the server may programmed to run scheduled SQL Server stored procedures to process the medical records and data into a final form for presentation in a patient website 22.

The server 18 may also create a database 94 which includes medical data 86 associated with the patient 78. The database 94 may facilitate storage and management of the patient data 86 and may facilitate the creation of a patient webpage 22. The database 94 may store medical information 86 for multiple patients 78 and may allow the easy access, sorting, management, and use of the medical information for the patients. The database 94 and the patient data 86 stored therein may be made available to hospital staff via a database interface and via a hospital computer 90.

The server 18 may create a patient webpage 22 from the medical records 82 (i.e. from the medical data 86 contained within the medical records 82). The database 94 may facilitate the creation of the patient webpage 22. As medical records 82 are created, the server may process the medical records to retrieve medical data 86. The medical data 86 may be added to the database 94 so that all medical data relevant to a patient 78 is stored in the database 94. The webpage 22 may be easily created by outputting the medical data 86 associated with a patient 78 from the database 94. In this manner, duplicative processing of medical records and data is avoided.

The patient webpage 22 thus may contain a detailed medical history of the particular patient 78 to which the webpage pertains. If desired, the medical data 86 may be filtered or edited in creating the patient webpage 22 according to the medical purpose for the webpage. For example, the issuance of the identification card 10 to a patient 78 may be predicated on the patient's particular medical condition. As such, particular data fields in the database 94 may be flagged as pertaining to that medical condition and the resultant patient webpage 22 may thus present patient information which is relevant to the prevailing medical condition. The patient webpage 22 may present information in a filtered manner such that information most relevant to the patient's medical diagnosis (54) is presented first or more prominently so that a doctor can view this information quickly in an emergency.

In creating the patient specific webpage, the patient medical data 86 may be processed to achieve certain functionality. For example, the patient medical data 86 may be processed for security purposes. Patient medical data 86 may be processed for the website 22 according to a security level for the website. Where the patient webpage 22 may be accessed publically, HIPPA prohibited information may be removed from the patient medical data 86 and thus not be displayed on the patient webpage 22. This type of information may be included in the database 94 as it may facilitate verification of the database for accuracy and use of the database internally at a hospital 14. This information may remain in the database 94 for use in the hospital 14, particularly where the database cannot be publically accessed. If HIPPA prohibited information is removed and not presented on a patient webpage 22, information such as the patient's name, date of birth, hospital admission date, etc. are not shown on the patient webpage. Where the patient webpage 22 requires authentication or is otherwise secured, additional patient information may be displayed on the webpage.

The patient medical data 86 may be processed to facilitate care of particular illnesses. Where a patient is treated for a particular medical condition 54, the server 18 may process the patient medical data 86 to extract, highlight, or prioritize certain data, medications, treatments, etc. which are particularly relevant to the medical condition 54. The patient webpage 22 may thus be structured according to a patient's medical condition 54. The server 18 may store patient webpage templates or data field lists that structure a patient webpage 22 differently according to the medical condition 54.

As an example of data processing, the server 18 may we use a SAS program to process medical records 82 and to process patient medical data 86. The server may be automatically scheduled to run at specified times to process medical records 82, process patient data 86, and create patient webpages 22. It will be appreciated that the server 18 may be programmed to operate differently according to the circumstances. For example, the server 18 may be programmed to process all selected medical records if a hospital 14 is first beginning to use the computer system and customer identification cards 10. Afterwards, the server 18 may be programmed to run at specified times during the day to process new medical records 82, add new patients 78 to the system, and create patient webpages 22. The server 18 may retrieve medical records 82 (in some cases from a medical records server) and process the medical records 82 to retrieve patient medical data 86 and normalize the patient medical data 86 into a database entry 94 or dataset.

In an example, the server 18 may create one database entry/record 94 per patient. The server 18 may be programmed to select patients for inclusion in the database 94 and in creating patient webpages 22. By default, the server 18 may be selected to include all patients seen within the past year, all patients who have elected to receive a patient identification card, etc. A medical record 82, database record 94, or other data record may be created to indicate if a patient has consented to receive a patient identification card and if the patient has been issued a card. In one example, the server 18 may process patient medical records for all relevant patients and may create a database record 94 for each patient. If the patient has received a patient identification card 10, the server 18 may output a patient webpage 22 corresponding to the patient. If desired, the server 18 may output patient webpages 22 to a dedicated web server. If the patient has not received a patient identification card 10, the server 18 may output a patient report corresponding to the patient for internal use at the hospital 14. The patient report may have a format which is similar to a patient webpage 22 and may be presented in an html format. If desired, the server 18 may output the patient report to an internal file server for staff use at a hospital 14.

The following examples are provided to illustrate how the server 18 may process different types of information found in patient medical records 82.

Demographics and diagnosis dataset: The server 18 may keep medical records numbers, patient name, gender, date of birth, diagnosis, the date the patient was last and first seen, allergies, blood type, and any patient introduction summary. The server may scan the medical records for protected health information (PHI) and create a True/False flag variable associated with the data field.

Physician list: The server may combine the physician and specialist mailing list fields from medical records into one row each containing the ID code, practitioner name, specialty and phone number. The server may combine the physician info with the demographics dataset based on practitioner ID#.

Patient physical information: The server may select the most recent height, weight and measurement date, and may calculate the patient body mass index (BMI).

The server 18 may process medical data differently depending on the patient's diagnosis. As an example, the server 18 may combine each patient's antibody test results into one condensed list per patient for patients with blood disorders. The server may combine the patient's antigen test results into one condensed list per patient. The server 18 may select and record the patient's most recent transfusion date and the corresponding pre and post transfusion hemoglobin. The server may determine the patient's current transfusion status.

If present, the server may select the most recent echocardiogram and keep the date, TRJet, LVEF, LVSF and PAP. The server may select the most recent SQUID and keep the date, liver volume, and liver iron concentration. If a cardiac MRI has been performed, the server 18 may select the most recent cardiac MRI and keep the date, T2* and LVEF.

It is thus appreciated that for certain types of tests and diagnosis, the history of various test results will be desired. For other tests and diagnosis, the results for the most recent test will be more relevant. The server 18 may have rules indicating how particular test data are processed.

Laboratory data: The server may select the most recent date and result for tests such as: hemoglobin, ferritin, platelets, white blood count, ANC, creatinine, total and direct bilirubin, ALT, AST, alkaline phosphatase, and LDH. The server 18 may create a separate dataset in the patient database entry for each test result.

Medications data: The server may combine variable numbers of medication records into one medication record per patient. The medication name, trade name, frequency and dose may be combined into one text block (data field). For medication data, as well as other medical data values, the server 18 may use HTML list-item tags which may be inserted at the beginning <li> and end </li> of each medication. When the final text output is created by the server 18, the medication section may be written out using unordered list tags <ul> and </ul> before and after the medication record containing the list-item tags.

Current medical issues and Past medical history: The server may condense each medical record into one string field per patient, keeping just the category and description.

Immunizations: The server may condense each immunization record into one string field per patient and vaccine type, listing the dates administered after each vaccine code.

These examples show different ways that the server 18 may process medical records and data found within the medical records according to the type of medical record and according to the type of data. In this manner, the server 18 may extract various pieces of data (datasets) from the patient medical records.

The server 18 may combine/merge all of the datasets into a single database record for each particular patient. The server 18 may merge information based on medical record numbers (i.e. a number associated with a particular patient found on each medical record). The final dataset (i.e. database record 94) may contain all PHI fields (including the exact date/times of lab results) and may be stored on a hospital internal file server such as server 18. Alternatively, the patient data 86, database data/record 94, webpages 22, etc. may be stored on external servers as necessary. For medical data, however, privacy is important and the location and access granted to data is typically associated with the type of data which may be permitted. The inclusion of complete patient data in the patient data 86 and/or database 94 may allow the system to easily change the data which is outputted to the patient webpages 22 according to the type of access which is granted and the nature of the security. Using a HIPPA compliant web application to display patient webpages 22 may allow the patient webpages to contain PHI.

For patients 78 who have elected to receive a patient identification card 10, the server 18 may create a patient identification number (patient ID or PID). The server 18 may create a random PID to use instead of a medical record number or other patient identification number to identify each patient and retrieve and display the patient webpage 22. The PID may be a randomly generated number so that the patient name or identification cannot be determined from the PID. The PID may contain a combination of random numbers, sequential numbers such as the sequence in which the server processed the patient application for the patient identification card, etc. As an example, the PID may include three digits of a random alphanumeric field plus a sequential record number converted to text data type; inserting a zero if the sequential records number is less than one hundred.

Patient confidentiality can be improved by creating a PID where the patient's identification cannot be determined from the PID. The PID may be used on the patient identification card 10 and on the patient webpage 22 and patient URL to safeguard the patient's identity. Where the URL for the patient webpage 22 is http://www.hospitalname.org/QR/[PID].html, for example, a person may gain access to various patient webpages 22 by entering a patient webpage (such as their own) and guessing different PID to gain access to different patient webpages. While the person may access different patient webpages, they would see patient medical data (such as a diagnosis, biological parameters, care protocols, etc.) without seeing any information which would identify the actual patient associated with the data. Thus, seeing a randomly selected patient webpage 22 would be akin to seeing a hypothetical case study for an unknown subject with a medical condition.

A SAS program may be used to automatically generate the QR codes which contain URL links using Proc Http and a Google web API, for example. The QR code may be generated to contain the patient website URL such that when scanned by a computer 30, the QR code directs the computer 30 to view the patient webpage 22 in an internet browser. The QR code may be generated as an image file, and these image files along with the other information presented on the patient identification card 10 may be imported into a database 94. The patient identification cards 10 may be printed as a "mailing label" type of report using a business card sized template which is convenient for the patient to carry and which is likely to be found if a doctor checks the patient for identification.

The server 18 may create a patient webpage 22 from the patient information 86 and/or patient database record 94. The server 18 may output simple HTML files to create the patient webpage 22. The patient webpage 22 may be stored in a patient webpage directory on the server 18 and may be saved as PID.html. If desired, the server may create an index page for internal hospital use containing the patient's name, diagnosis, date of birth, and report links such as a URL link to the patient's web report, and URL links to their treatment protocols and supplemental information. The server 18 may output the HTML index to an in-house file server if desired. The server 18 may use a "data_null_" step and "put" statements, loop through the patient medical record data by medical record number and output a text file with an .html extension. Alternatively, the server 18 may retrieve the data from the patient database record 94 and create a text file with an .html extension for display as the patient webpage. The server 18 may insert the HTML Header section (Doctype, title, meta tags, CSS).

The server 18 may prepare an HTML Body section. The server 18 may insert paragraph and header tags to format the data into sections such as: Demographics, Allergies, Introduction, Medications, Laboratory and imaging results, Active Problems, Past Problems, Immunizations, and Physician list. The HTML code and data variables may be interspersed within each output line.

In creating the patient database record 94 or in creating the patient webpage 22, the server 18 may combine patient data with protocol care links based on the patient's medical diagnosis 54. The server 18 may store a list of care protocols for different medical conditions 54. The care protocols may address specific patient types, specific patient conditions or diagnosis, and treatment specific to care of such a patient. A transport care protocol may thus be specific to children or specific to adults, as these may have different needs for medical treatment. The care protocols may thus provide guidance to doctors in understanding the patient's condition 54 and in caring for that patient. The care protocols may assist a doctor in providing appropriate treatment to the patient based on the conditions for the patient. The care protocols may be of particular assistance to a doctor where the patient has a rare, complex, or chronic condition which is not well understood by a doctor who does not specialize in this condition.

The server 18 may store html links to the care protocols, and may organize care protocols into simple html pages which can be displayed to a doctor. The html pages may be simple text based pages so that they may be displayed effectively and quickly on many electronic devices. The server 18, in processing the medical records 82, extracting patient data 86, creating a patient database record 94, or in creating a patient webpage 22 may insert html links into the data such that html links to care protocols are provided as part of the patient webpage 22. The server 18 may select care protocol links which are appropriate for the patient's medical condition 54 and which are appropriate for the patient's age, etc. As a doctor views the patient webpage 22, the doctor may select the care protocol links 22 and view care protocols and guidance in treating the patient in addition to the patient data displayed on the patient webpage 22.

In creating the patient webpage 22, the server 18 may insert contact information and instructions to assist the doctor in contacting the doctor or hospital 14 which primarily treats the patient. The server 18 may insert instructions to call the hospital 14, and may also add a contact link or contact information to the appropriate doctor on-call and primary care doctor. The contact information for these doctors may be retrieved from a hospital and doctor contact database stored within the server 18. In creating the patient webpage 22, the server may insert an HTML footer section as needed.

If desired, the patient webpage 22 may be programmed to include toggle buttons (+ or − buttons) or similar links which toggle between displaying and not displaying particular categories of information. This allows a user to quickly review the contents of the patient webpage 22 and access or hide information as desired instead of requiring the user to scroll through the page. These toggle buttons/links could toggle between displaying or hiding sections such as "Lab Results", "Medications", "Treatment Data" and the like.

In creating a patient webpage 22, the server 18 may scan the final dataset for any remaining PHI and if any is found, the webpage 22 may be flagged for staff review and sent to an in-house file server only. PHI may appear in clinical summaries or other locations where it may be found within text and not identified as a PHI field while the server 18 is processing medical records 82 or data 86.

It is desirable that the information presented on the patient webpage 22 is up to date. The computer system may update the patient webpage 22 often due to changes in patient data and due to predetermined schedules. For example, the server 18 may be programmed to process new medical records 82 at different times during the day and processing a patient medical record 82 may trigger an updated patient webpage 22. The server 18 may be programmed to process new medical records 82 as they are created. New medical records 82 may be added to a queue and processed as created, or processed at predetermined times throughout the day. As the medical records 82 are processed, the server 18 may be programmed to add the extracted medical data 86 to a patient database record 94. If a database record 94 is not used, the server 18 may be programmed to update the patient webpage 22 as a relevant patient medical record 82 is processed.

The server 18 may be programmed to update the patient webpage 22 at predetermined intervals or as data is added to a patient database record 94. If processing a medical record 82 results in updating a patient database record 94, the patient database record (corresponding to the patient) may be added to a queue and the patient webpage 22 associated with that patient and patient database record 92 may be updated by the server 18.

The server 18 may be programmed to update the patient webpage 22 if necessitated by other changes outside of patient medical records 82 or data 86. For example, the patient webpage 22 may display hospital, primary care doctor, and on-call doctor contact information. The server 18 may thus be programmed to periodically update the patient webpage 22 as these contacts change so that the webpage has updated contact information. Additionally, the server 18 may be programmed to periodically update the patient webpages 22 independent of any data driven updates. In this way, the patient webpage 22 may be always up to date.

If a patient identification card 10 is lost or otherwise compromised, the server 18 may simply assign a new PID to the patient and associate the PID with the patient. Processing patient medical records 82 will then associate the medical data 86 to the new PID. The patient database record 94 may be updated with the new PID so that the data is maintained and so that the database record is updated with new data 86. At the next triggered update (or an immediately triggered update), the server 18 may create a new patient webpage 22 with the new PID as part of the URL and the old patient webpage 22 may be deleted. A new patient identification card 10 with the new patient webpage URL and machine readable code may be created and sent to the patient.

Certain tasks, such as processing medical records 82 to retrieve patient medical data 86 may be complex and computationally expensive. As such, these tasks may be performed only as needed; or only once per medical record 82. The medical records 82 may be processed as they are created and incorporated into the system. The server 18 may process medical records 82 once and output and save medical data 86 or a database record 94. Other tasks, such as creation of a text based webpage 22 from a patient database record 94 may be computationally inexpensive and easily performed by the server 18. As the patient webpages 22 may be static web pages with simple html text and minimal graphics, these webpages may be continually re-generated throughout the day as the server 18 updates the patient webpages according to a desired schedule. Thus, the server 18 may be able to update the patient webpage 22 by outputting a patient database record 94 to a simple text based html webpage 22 periodically as desired. Simple text based html is easy to create and quickly updated and is quickly downloaded by a doctor and quickly navigated to gain information about a patient and provide care to that patient.

Figure 4:
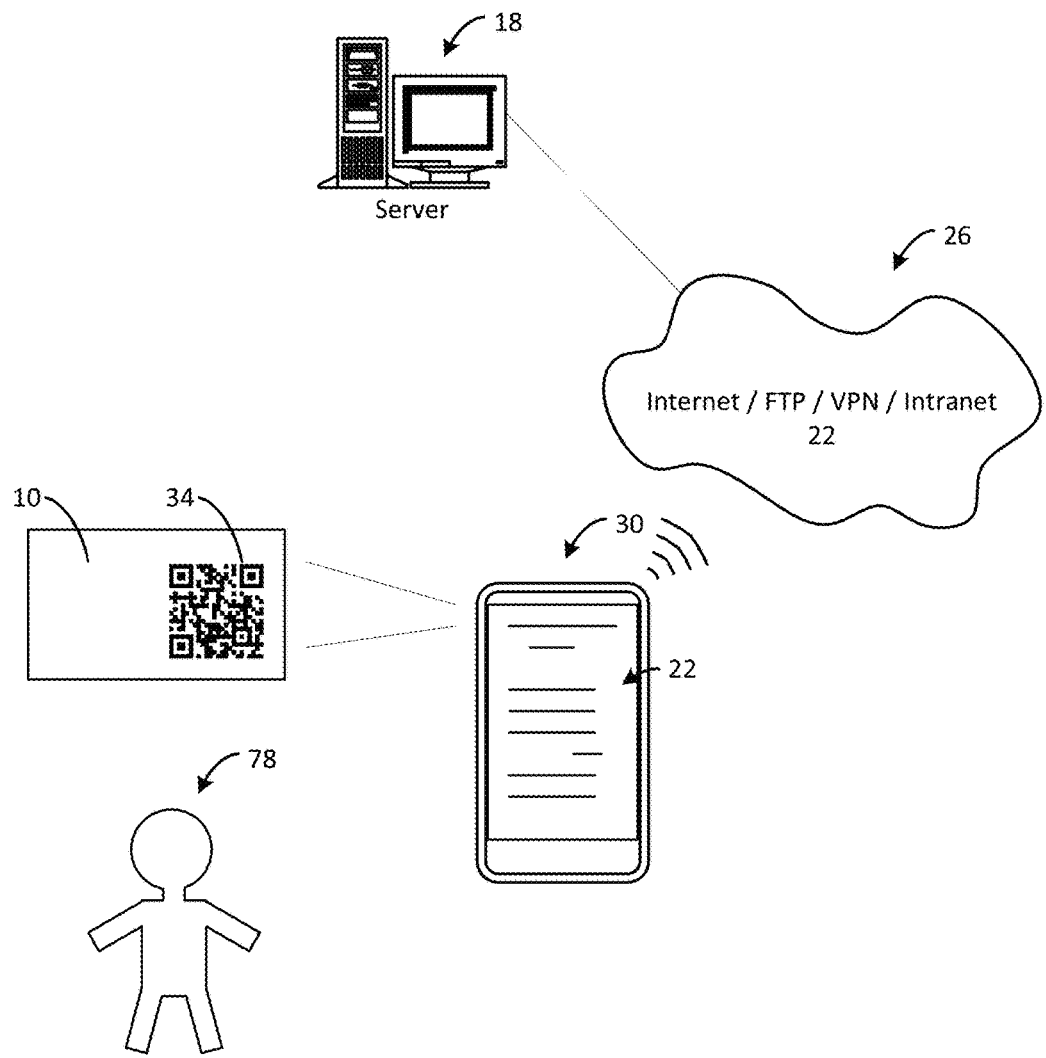

Referring now to FIG. 4, a patient 78 may carry a patient identification card 10. The patient 78 may be in need of medical care, such as when the patient presents themselves at a medical facility or if a medical emergency occurs with the patient. A doctor may desire to help the patient 78 by providing medical care to the patient. The doctor may discover or the patient may present to the doctor a patient identification card 10. The doctor may have a computer such as a portable electronic device 30. The electronic device 30 may include software and hardware to scan machine readable codes such as QR codes, as well as software and hardware to retrieve and view internet webpages. The electronic device 30 may thus scan the machine readable code 34 on the patient identification card. The electronic device 30 may have software specific to the patient identification cards 10 and associated system which receives information from the code 34 and retrieves the patient webpage 22. Alternatively, the machine readable code 34 may be created to work with any scanning software which can scan a machine readable code and retrieve a webpage in response thereto. This may permit many doctors to better assist the patient 78 without having first installed a specific application to retrieve the patient webpage 22.

The electronic device 30 may receive, from the machine readable code, instruction to retrieve and display a patient webpage 22 corresponding to the patient. The electronic device 30 may then retrieve the patient specific webpage 22 and display the webpage on an internet browser. More specifically, the electronic device 30 may contact the server 18 via the internet 26 to request the patient webpage 22 corresponding to the PID encoded into the QR code 34 and the patient webpage URL. The server 18 may transmit the patient webpage 22 to the electronic device 30. The patient specific webpage 22 may be a simple text based webpage which is retrieved and displayed quickly. The electronic device 30 may display to the doctor the patient webpage so that the doctor may read the patient webpage. The doctor thus learns of a particular medical condition which afflicts the patient. The doctor may also select html links within the patient webpage 22 and the electronic device 30 may display other webpages which present additional care protocols for the medical condition 54 which afflicts the patient 78. The electronic device 30 thus provides detailed patient information to the doctor to allow the doctor to provide better care to a patient who may require a specialized degree of care.

Figure 5:
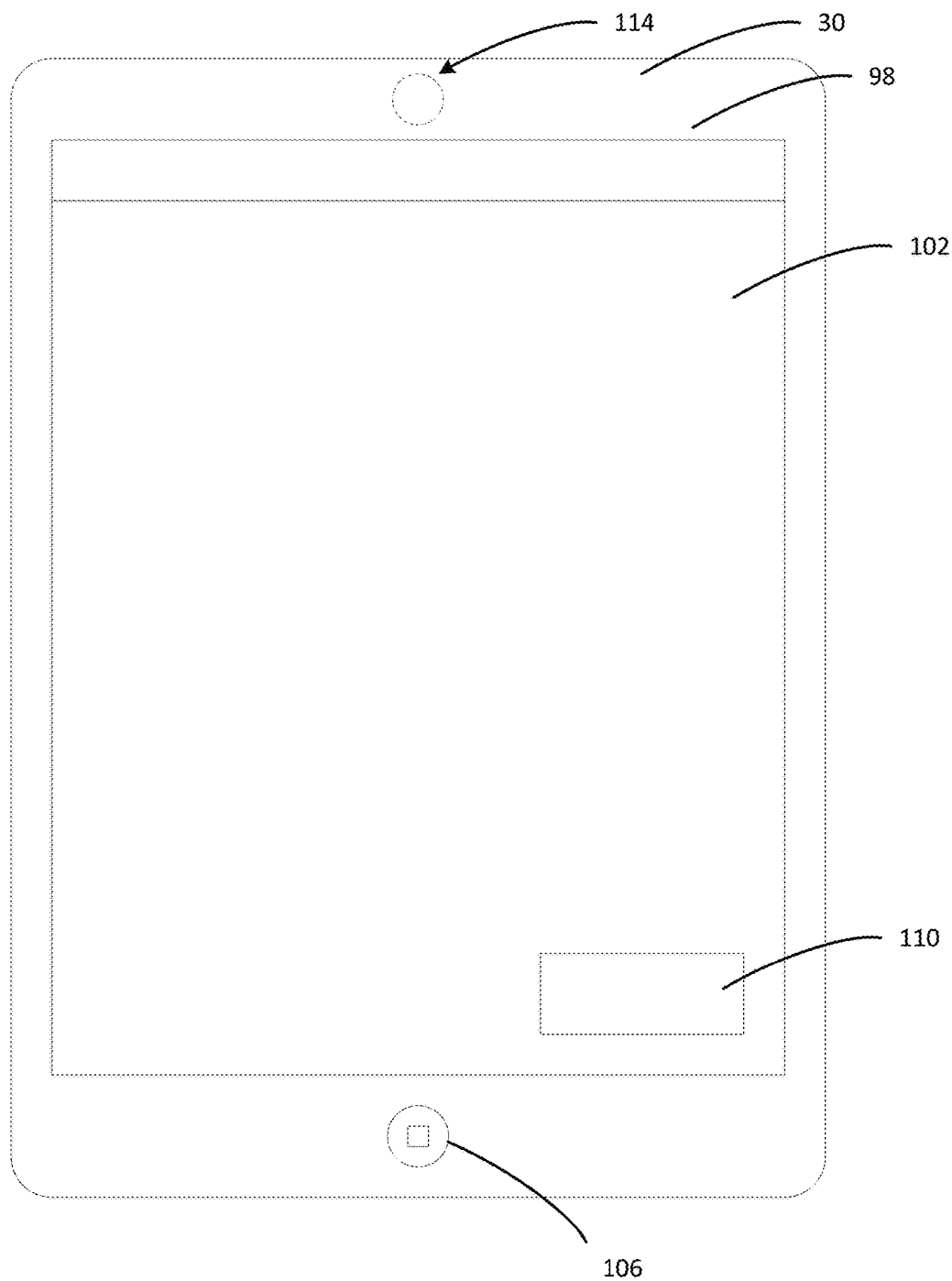
FIG. 5 shows a computer used to display patient information.

Referring to FIG. 5, the computer 30 (smart phone, tablet computer, laptop, desktop computer, etc.) typically includes a body or case 98 which houses internal electronic s such as a processor, memory, battery, wireless communications device, etc. The computer 30 includes a user interface such as screen 102. Typically, the screen 102 is a display screen which presents information to a user and, in many instances, may also be a touch screen which accepts inputs from a user to allow the user to control the computer 30. The computer 30 may include various hardware buttons 106 which allow a user to operate the device, navigate through menus, etc. The computer 30 may include various software buttons 110 which allow a user to select software, change software or hardware settings, etc. The computer 30 may also include a camera 114. The various components of the computer 30 allow the computer 30 to perform the functions and display the data discussed herein.

Figure 6:
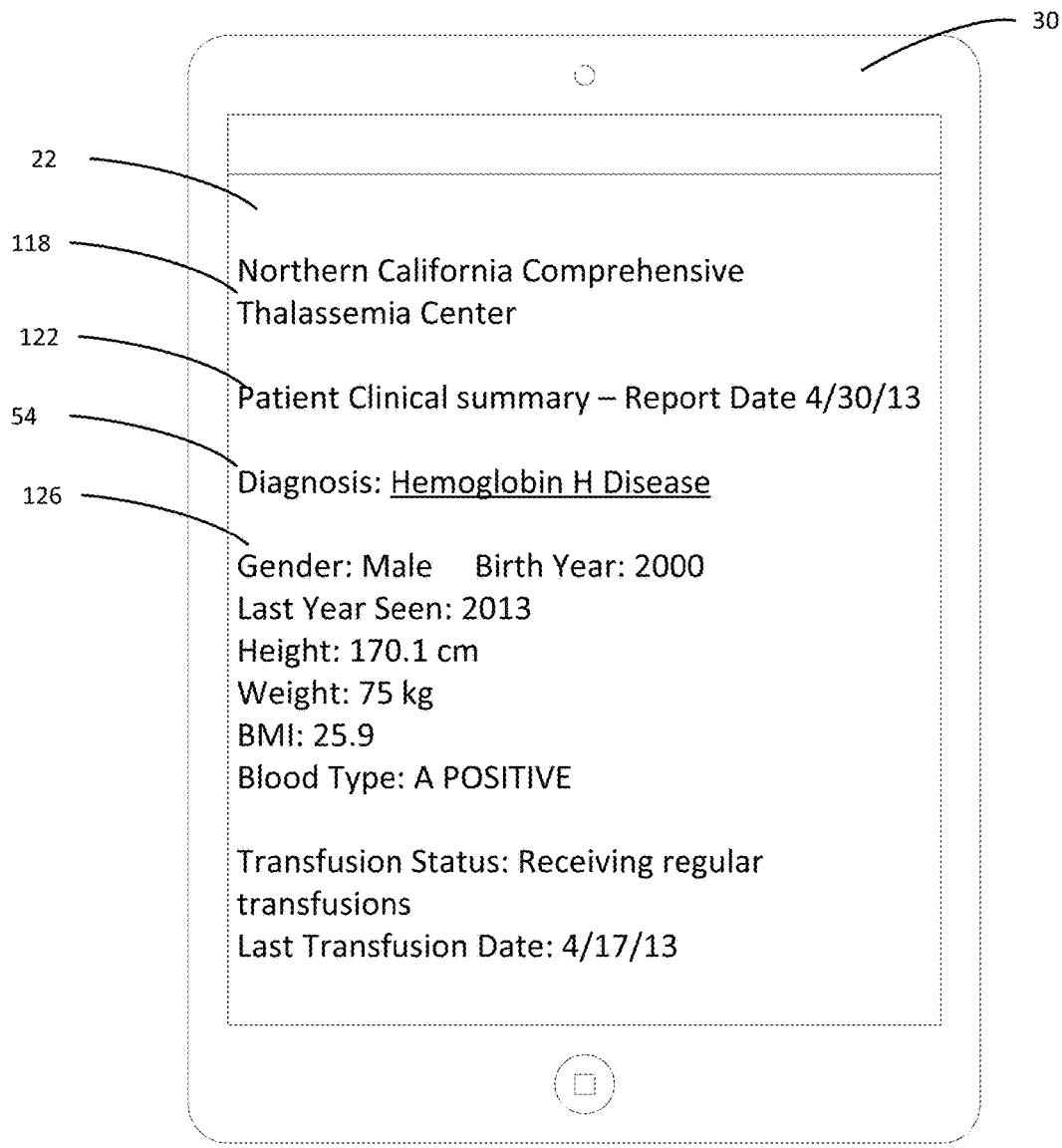
FIGS. 6 and 7 show a personalized patient website displayed on a mobile electronic device.
Figure 7:
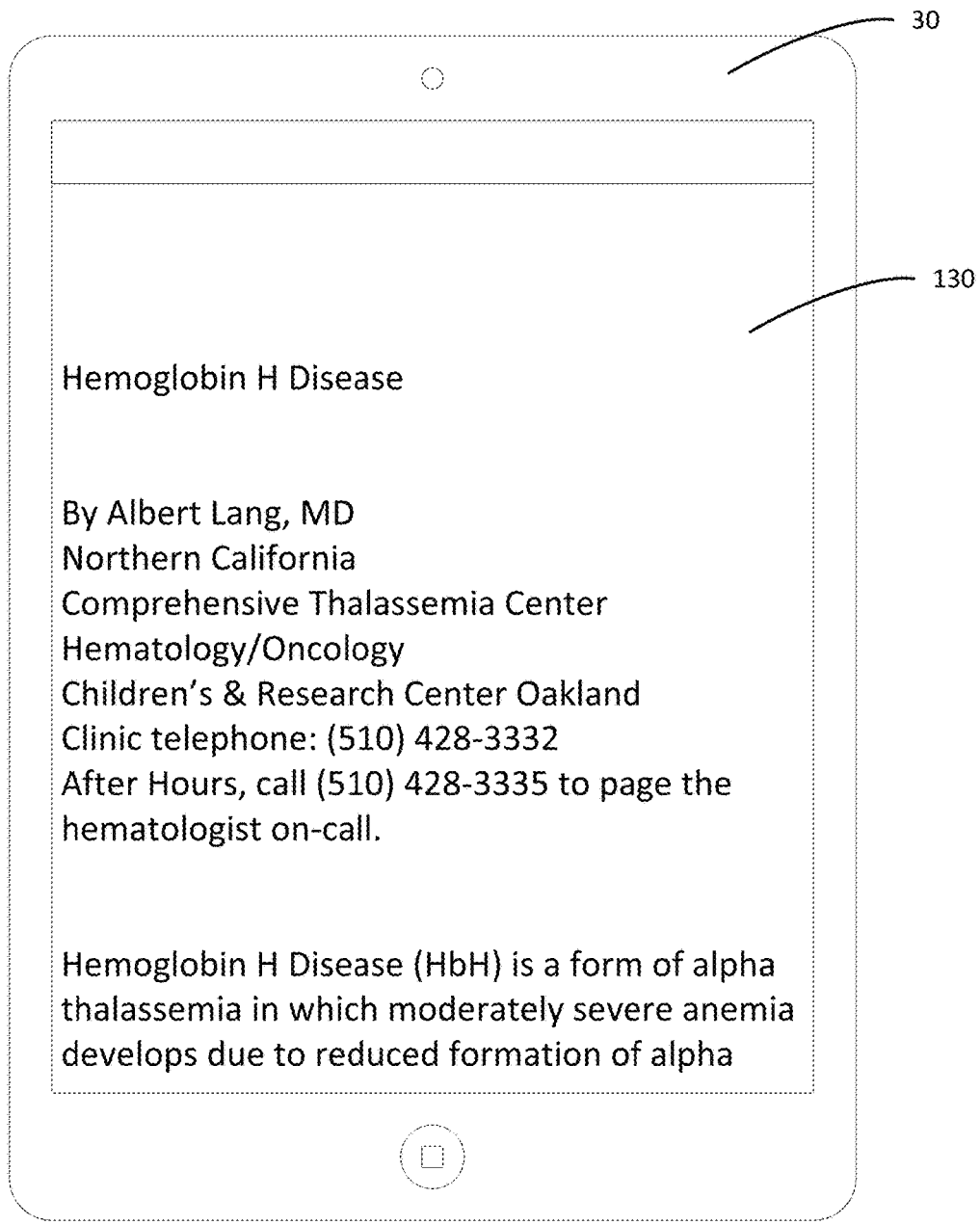

Referring now to FIGS. 5 and 6, drawings of a computer such as a portable electronic device 30 displaying a patient webpage 22 and associated information are shown. The patient webpage 22 may display the hospital name 118 which primarily treats the patient 78. The webpage 22 may also display a title 122 which indicates to the doctor that the webpage displays a clinical summary or patient information. The webpage 22 may display the patient diagnosis 54. As an example, the diagnosis text may be an internet link which, if selected, displays a summary page 130 (FIG. 6) of the particular medical condition 54. The patient webpage 22 may also display patient physical data 126. Although not shown, the patient webpage 22 may display patient test results, clinical summaries, medications, and other information relevant to ongoing treatment of a patient with the medical condition 54. The patient webpage 22 and/or diagnosis summary page 130 may also include internet links which, when selected, cause the device 30 to display webpages which display care protocols, provide additional information regarding the medical condition, and provide guidance for treating the patient.

As the patient webpage 22 displays accurate patient specific information to assist in treating the patient, it is typically desirable to ensure that the patient's webpage 22 is not cached in the electronic device 30 and that a fresh copy of the webpage is always retrieved from the server 18 each time it is requested. Otherwise, the patient information such as labs, medications, etc. could be out of date. Additionally, contact information such as the doctor-on-call that evening that a doctor may contact to seek guidance in caring for the patient 78 may be out of date. The patient webpages 22 may be programmed to expire after a time period following retrieval of the webpage. This may cause the electronic device 30 to retrieve a new copy of the webpage 22. Alternatively, dynamic web pages may be used instead of HTML (i.e. ASP.NET pages with .aspx extension) to ensure that an up to date copy of the webpage is viewed. If a dynamic webpage was used, the webpage code could include logic to check the current time of day and automatically set the correct contact information (for a hospital or clinic or on-call doctor) for the contact information or for a 'click to call us' link. In many situations, however, it is desirable to keep the webpage simple in order to allow the webpage 22 to load as fast as possible and to be compatible with every type of electronic device 30.

The patient webpage 22 may include additional features to facilitate care of the patient 78. For example, the patient webpage 22 may include internet links to scanned PDF copies of medical powers of attorney or patient advanced directives. As these documents are likely to contain PHI, access to these documents could be restricted through the use of an authentication code, password, or PIN number. An embedded finger print reader could be used to permit access to these pages.

If desired, a mobile latitude/longitude geolocation function combined with organization-level web log analysis may be used to implement utilization tracking. The server 18 may track usage of the patient identification cards 10 via software such as Windows® IIS Server logs and WebLog Expert Software. Software such as these will show when and where a patient's card 10 was scanned and the patient webpage 22 was accessed. Since mobile electronic devices 30 may be using a cellular data provider rather than institutional Wi-Fi to access internet data, it may not be possible to know which medical center viewed the patient webpage 22 just relying on the web logs. Addition of a Geolocation function allows the server 18 to pinpoint latitude and longitude where the webpage 22 was accessed and use a database of medical center locations to determine which hospital or medical institution accessed the webpage 22. The server 18 may use this information to ensure a patient's identification card 10 has not been lost and is not being misused, as well as to track the usage and effectiveness of the system.

Every time the URL is accessed, the server 18 may generate an automatic message to the primary care doctor to notify that the patient may be receiving medical treatment. This may allow the primary care doctor to follow up with a patient regarding the medical care and their health status and may allow the primary care doctor to communicate with the doctor currently providing care to the patient. In this manner, the server 18 will involve the primary care doctor and keep them informed about the treatment being provided to the patient 78.

Various security protocols may be implemented to improve the usefulness of the patient identification cards 10. Since medical information is legally protected, increased security in displaying the patient webpages 22 may allow additional information to be provided to a doctor viewing the webpages. If a security system ensures that the patient webpage 22 is viewed by a doctor and/or at the (sometimes implied) request of the patient, PHI may be displayed on the patient webpage 22.

In one example, a fingerprint sensor may be used as a security measure. The server 18 may store fingerprint information for the patient 78 and a patient fingerprint scan may be required to access the patient webpage 22. This would ensure that the patient 78 is present when the patient webpage 22 is accessed. The fingerprint scan may be implemented as a hardware or software module on the mobile electronic device 30. Alternatively, an embedded fingerprint scanner may be included as part of the patient identification card as discussed above. Successfully scanning the patient fingerprint on the embedded scanner may display an access code to allow the patient webpage 22 to be retrieved.

Similarly, an iris scan may be used as a security measure. The server 18 may store iris information for the patient 78 and a patient iris scan may be required to access the patient webpage 22 in order to ensure that the patient 78 is present when the patient webpage is accessed. The iris scan may be implemented as a hardware or software module on the mobile electronic device 30, for example. A camera on the mobile electronic device 30 may be used to capture an image of the patient's iris and the server 18 may analyze the captured image against the stored iris information to verify that the captured image is an image of the patient's iris. Successful verification may permit the doctor to access the patient webpage 22. Similarly, the server may store iris information for doctors authorized to access the patient webpages and may require successful authentication by a doctor (i.e. capturing an image of the doctor's iris and comparing the image against the server data) in order to permit the doctor to access the patient's webpage 22.

If desired, a doctor fingerprint scan or authentication code may be required to access the patient webpage 22. The electronic device 30 may require software to scan the machine readable code 34, supply doctor security credentials, and retrieve the patient webpage 22. A doctor may be required to provide proof of licensing (medical license number or registration number) in order to obtain or install the software. The server 18 may verify the proof of licensing, or staff may verify the proof of licensing in order to validate the doctor's account. The doctor may be required to supply a finger scan to the server 18 or provide a PIN number or authentication code to the server 18 and may create a user account with the server 18. The doctor may then be required to scan their fingerprint on a fingerprint sensor implemented in a mobile electronic device 30 (such as a power button on a phone or tablet computer or a fingerprint scanner on a laptop or tablet computer) in order to retrieve and view a patient webpage 22. This would ensure that the doctor is a licensed medical professional and that it is in fact the doctor who is using the mobile electronic device 30 to access the patient webpage.

If desired, a patient access code may be required to access the webpage 22. If the patient 78 must provide an access code, the patient would necessarily be present and consenting to the patient webpage 22 being accessed.

As another alternative, scanning the machine readable code 34 or entering a corresponding URL into the electronic device 30 may cause the server 18 to present an authentication page on the electronic device. The authentication page may request that the doctor take a photo of the patient's face with the device's camera. Facial recognition software on the server 18 may compare that photo to a securely stored photo of the patient and determine if it was a match without showing the stored photo. If the match was positive, the patient's webpage 22 would be transmitted to the device 30.

Security may be enhanced by requiring a secure https connection and a user ID and password. The user ID and password may be encoded in the QR code 34 so that they do not have to be typed in manually.

It is also possible to increase security by removing the patient's name 38 from their identification card 10. A partial photo of the patient's face, such as a photo of their nose or eyes, could be included in the patient's webpage 22 which could be used by the physician to verify the patient's identity on a de-identified webpage 22 with a de-identified identification card 10.

With security measures in place to verify that a doctor is accessing the patient webpage 22 or that the patient 78 is present while accessing the webpage 22, additional PHI may be displayed and be available to the doctor for use in treating the patient. As an example, full patient charts could be provided to the doctor.

Figure 8:
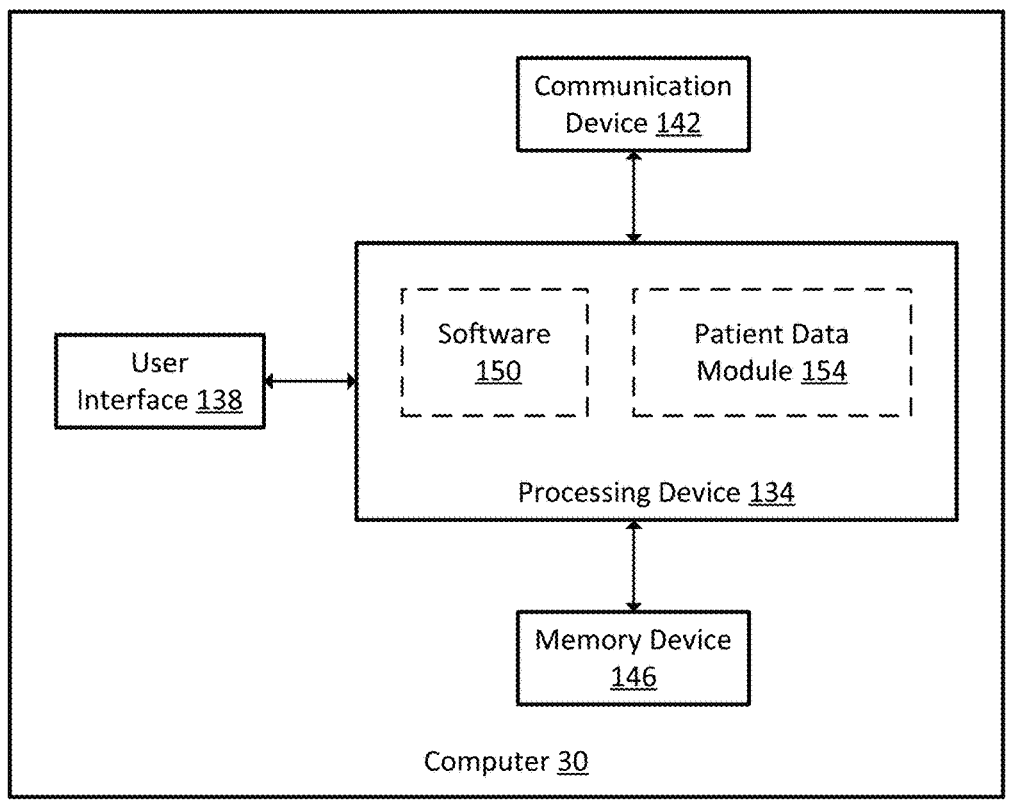
FIG. 8 is a schematic illustrating example components of the mobile electronic device or computer.

Referring now to FIG. 8, a schematic illustrating example components of the computer 30 is shown. As discussed, the computer 30 may be a smart phone, tablet computer, laptop computer, desktop computer, etc. Frequently, the computer 30 will be a smart phone or tablet computer which is capable of receiving and displaying internet data and webpages. The computer 30 includes a processing device 134, a user interface 138, a communication device 142, and a memory device 146. It is noted that the computer 30 can include other components and some of the components are not required.

The processing device 134 can include memory, e.g., read only memory (ROM) and random access memory (RAM), storing processor-executable instructions and one or more processors that execute the processor-executable instructions. In embodiments where the processing device 134 includes two or more processors, the processors can operate in a parallel or distributed manner. The processing device 134 can execute the operating system of the computer 30. In one example, the processing device 134 also executes a software module 150 and a patient data module 214.

The user interface 138 is a device that allows a user, a doctor in particular, to interact with the computer 30. While one user interface 138 is shown, the term "user interface" can include, but is not limited to, a touch screen, a physical keyboard, a mouse, a camera, a microphone, and/or a speaker. The communication device 142 is a device that allows the computer 30 to communicate with another device, e.g., the server 18. The communication device 142 can include one or more wireless transceivers for performing wireless communication and/or one or more communication ports for performing wired communication. The memory device 146 is a device that stores data generated or received by the computer 30. The memory device 146 can include, but is not limited to, a hard disc drive, an optical disc drive, and/or a flash memory drive.

The patient data module 154 allows a user, a doctor in particular, to receive patient data which is specific to a particular patient in response to entering a PID in the form of a URL associated with a patient personalized webpage 22. The patient data module allows a doctor to receive personalized patient information for a patient 78 and perform various tasks in caring for a patient as discussed herein. The patient data module 154 may execute or facilitate internet communications and may retrieve and display patient specific medical data and patient care protocols as discussed herein.

Figure 9:
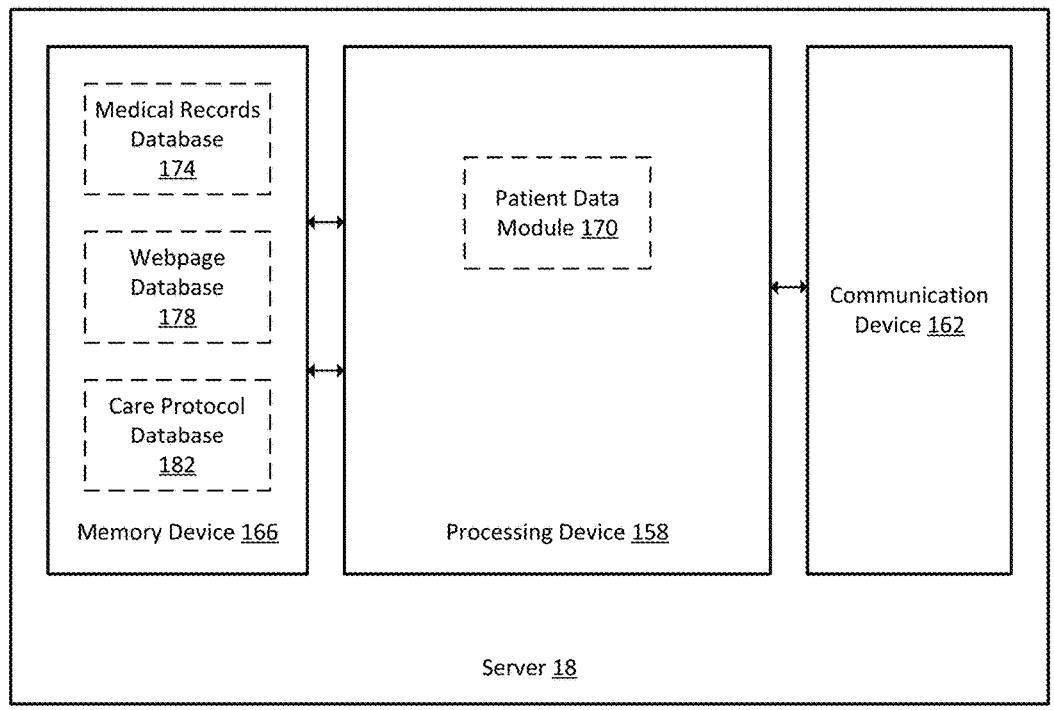
FIG. 9 is a schematic illustrating example components of a server.

The server 18 may be programmed to perform one or more functions at the request of the computer 30 and, according to various computing models, may execute some or all of the functions associated with operation of the patient data module. FIG. 9 illustrates an example embodiment of a server 18 which is programmed to perform one or more of the requested functions. The server 18 may include a processing device 158, a communication device 162, and a memory device 166.

The processing device 158 can include memory, e.g., read only memory (ROM) and random access memory (RAM), storing processor-executable instructions and one or more processors that execute the processor-executable instructions. In embodiments where the processing device 158 includes two or more processors, the processors can operate in a parallel or distributed manner. In the illustrative embodiment, the processing device 158 executes a patient data module 170. The patient data module 170 may execute, process, or facilitate internet communications, patient records, patient data, a database, patient care protocols, etc. as discussed herein.

The communication device 162 is a device that allows the server 18 to communicate with another device, e.g., the computer 30. The communication device 162 can include one or more wireless transceivers for performing wireless communication and/or one or more communication ports for performing wired communication.

The memory device 166 is a device that stores data generated or received by the server 18. The memory device 166 can include, but is not limited to a hard disc drive, an optical disc drive, and/or a flash memory drive. Further, the memory device 166 may be distributed and located at multiple locations. The memory device 166 is accessible to the processing device 158. In some embodiments, the memory device 166 stores data such as a patient medical records database 174, a patient webpage database 178, and a care protocol database 182.

In some embodiments, the patient medical records database 174 can store information associated with a patient such as medical records, medical data, etc. The patient medical records database 174 may be queried by the processing device 218 and may provide information to the processing device to facilitate the processing of medical records, processing of patient data, and creation of patient webpages 22.

The patient webpage database 178 may store information regarding patient personalized webpages 22. The patient webpage database 178 may store a plurality of patient webpages 22. The patient webpage database 178 may be queried by the processor 158 to retrieve a patient webpage 22 and display the patient webpage 22 on a computer 30.

The care protocol database 182 may store information regarding specific medical conditions and information regarding care protocols and care tasks associated with treatment of a patient with a specific medical condition. The care protocol database 182 may be queried by the processing device 158 and may transmit information to the processing device to display information regarding a medical condition on a computer 30 to facilitate the care of a patient with a rare, complex, or chronic medical condition.

The processing device 158 may execute the patient data module 170. The patient data module 170 may receive and process patient information such as patient medical records 82 to extract patient medical data 86 and create patient webpages 22 as well as to provide patient webpages 22 to the computer 30, etc. The patient data module 170 may transmit information regarding patient data, prior care of the patient 78, and care protocols related to the patient 78 to the computer 30 and facilitate the care of a patient 78 with a rare, complex, or chronic medical condition by any doctor as though the patient was receiving care from a specialist primary care provider.

The computer system is advantageous as it does not require any additional hardware to implement. The system can be implemented on an existing hospital server 18. The computer system may be implemented on existing mobile electronic devices with only software. The webpage output may be simple html and may thus be device independent and provide good performance even where little internet data bandwidth is available. The computer system also does not require any additional hardware on the user side. A user can utilize the computer system and access patient webpages 22 with only a smartphone, tablet computer, etc. and a free, widely available QR scan code application. With minimal cost to implement the system, access to detailed medical information is provided to a doctor to allow the doctor to appropriately care for a patient. The system is particularly useful in the context of rare, complex, and chronic medical conditions where treatment typically requires specialization and knowledge of the particular patient.

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention. Indeed, it is appreciated that the specific example voltages, currents, frequencies, power range values, times, etc., are provided for explanation purposes and that other values may also be employed in other embodiments and examples in accordance with the teachings of the present invention.

What is claimed is:

1. A method comprising:
   retrieving, by a server computer system, patient medical records pertaining to a patient;
   processing, by the server computer system, the patient medical records to extract patient medical data pertaining to the patient, wherein said processing includes, by the server computer system,
     accessing medical record datasets of a plurality of different types, associated with the patient,
     identifying one or more first data fields in the medical record datasets as being relevant to a particular medical condition of the patient,
     identifying one or more second data fields in the medical record datasets as having been classified as being classified as sensitive or protected information,
     flagging the identified first data fields and the identified second data fields for subsequent processing, and
     merging at least portions of the medical record datasets of the plurality of different types, including the flagged first data fields and second data fields, into a single database record for the patient;
   creating, by the server computer system, a patient webpage specific to the patient from the single database record for the patient, the patient webpage including the patient medical data, wherein said creating the patient webpage includes creating the patient webpage to include the one or more first data fields in the patient webpage and to omit the one or more second data fields from the patient webpage, based on said flagging;
   providing a wallet-size patient identification card associated with a patient, the patient identification card including a processor, an embedded fingerprint scanner, a memory to store a fingerprint of the patient, and a display device, the patient identification card further having an indicator disposed thereon, the indicator being a network resource locator corresponding to the patient webpage or a machine-readable code representing the network resource locator corresponding to the patient webpage;
   receiving, by the server computer system, from a second computer, a request corresponding to the network resource locator, the request having been sent by the second computer in response to the second computer having received as input the network resource locator or an image of a machine readable code corresponding to the network resource locator, the request having been sent by the second computer in connection with the patient being treated by or seeking treatment or advice from a first health care provider other than a primary care physician of the patient;
   the processor of the patient identification card being configured to cause the embedded fingerprint scanner of the wallet-size patient identification card to acquire a fingerprint of a person and to compare the acquired fingerprint to a stored fingerprint of the patient stored in the memory and, when the acquired fingerprint matches the stored fingerprint, to cause a personal identifier to be displayed on the display device of the patient identification card;
   receiving the personal identifier at the server computer system from the second computer system, after the personal identifier is provided as input to the second computer by a user in response to display of the personal identifier by the display device of the patient identification card;
   determining, by the server computer system, whether the personal identifier is correct;
   in response to determining that the personal identifier is correct, transmitting, by the server computer system, the patient webpage to the second computer; and
   in response to the network resource locator being accessed in connection with the patient being treated by or seeking treatment or advice from the first health care provider other than the primary care physician of the patient, automatically generating a notification message to the primary care physician of the patient, indicative that the patient webpage has been accessed, wherein the patient webpage is not owned or controlled by the first health care provider or the primary care physician of the patient.

2. The method of claim 1, wherein the patient webpage comprises a patient diagnosis of a medical condition and patient clinical data pertaining to the condition.

3. The method of claim 1, wherein the webpage contains links to treatment protocols for the patient diagnosis.

4. The method of claim 1, further comprising:
   in response to the request, causing, by the server computer system, the second computer to output a prompt for a user of the second computer to acquire a photograph of a face of the patient;
   receiving, by the server computer system, a photograph of the face of the patient, the photograph having been acquired as a result of the user responding to the prompt; and
   determining, by the server computer system, whether the photograph of the face of the patient corresponds to a stored photograph of the face of the patient.

5. The method of claim 1, further comprising:
   receiving, at the server computer system, geolocation data associated with the patient identification card; and
   verifying that the patient is in possession of the patient identification card by analyzing the geolocation data associated with the patient identification card, before transmitting the patient webpage to the second computer system.

6. The method of claim 1, further comprising:
   incorporating into the patient webpage a link to a care protocol associated with a medical condition that is associated with the patient.

7. A method comprising:
retrieving, by a server computer system, patient medical records pertaining to a patient;
processing, by the server computer system, the patient medical records to extract patient medical data pertaining to the patient and to create a database record for the patient, the database record containing the patient medical data pertaining to the patient;
creating, by the server computer system, a patient webpage specific to the patient, based on the database record, the patient webpage including the patient medical data;
providing a patient identification object associated with a patient, the patient identification object having a physical form that enables the patient identification object to be carried on the body or in clothing or a personal accessory of a person, the patient identification object including a processor, an embedded fingerprint scanner, a memory to store a fingerprint of the patient, and a display device, the patient identification object further having an indicator, the indicator being a network resource locator corresponding to the patient webpage or a machine-readable code representing the network resource locator corresponding to the patient webpage;
receiving, by the server computer system, from a second computer, a request corresponding to the network resource locator, the request having been sent by the second computer in response to the second computer receiving as input the network resource locator or an image of a machine readable code corresponding to the network resource locator;
the processor of the patient identification object being configured to cause the embedded fingerprint scanner of the patient identification object to acquire a fingerprint of a person in possession of the patient identification object and to compare the acquired fingerprint to a stored fingerprint of the patient stored in the memory and, when the acquired fingerprint matches the stored fingerprint, to cause a personal identifier to be displayed on the display device of the patient identification object;
receiving the personal identifier at the server computer system from the second computer system;
determining, by the server computer system, whether the personal identifier is correct;
in the event that the personal identifier is determined to be correct, transmitting, by the server computer system, the patient webpage to the second computer in response to the request; and
periodically updating the patient webpage, for display, during a day to contain contact information for an on-call doctor at a hospital primarily responsible for treating the patient, wherein the on-call doctor is not a primary care physician of the patient.

8. The method of claim 7, wherein the patient identification object is a wallet-size card.

9. The method of claim 7, further comprising:
in response to the request, causing, by the server computer system, the second computer to output a prompt for a user of the second computer to acquire a photograph of a face of the patient;
receiving, by the server computer system, a photograph of the face of the patient, the photograph having been acquired as a result of the user responding to the prompt; and
determining, by the server computer system, whether the photograph of the face of the patient corresponds to a stored photograph of the face of the patient.

10. The method of claim 7, wherein extracting the patient medical data comprises, by the server computer system:
accessing medical record datasets of a plurality of different types, associated with the patient; and
merging at least portions of the medical record datasets of the plurality of different types, into the database record for the patient.

11. The method of claim 7, wherein extracting the patient medical data comprises, by the server computer system:
accessing medical record datasets of a plurality of different types, associated with the patient; and
identifying one or more first data fields in the medical record datasets as being relevant to a particular medical condition of the patient;
flagging the identified first data fields for subsequent processing; and
merging at least portions of the medical record datasets of the plurality of different types, including the flagged first data fields, into the database record for the patient;
wherein said creating the patient webpage includes creating the patient webpage to include the one or more first data fields in the patient webpage.

12. The method of claim 11, wherein extracting the patient medical data comprises, by the server computer system:
identifying one or more second data fields in the medical record datasets as having been classified as being classified as sensitive or protected information,
flagging the identified second data fields for subsequent processing,
wherein said merging further comprises merging the flagged second data fields into the database record for the patient, and wherein said creating the patient webpage includes creating the patient webpage to omit the one or more second data fields from the patient webpage, based on said flagging.

13. The method of claim 7, wherein the method further comprises processing, by the server computer system, new medical records according to a specified periodicity to update the patient webpage.

14. The method of claim 7, wherein the medical data comprises information regarding treatment of the patient for a particular medical diagnosis.

15. The method of claim 7, wherein the method further comprises verifying that a doctor is in possession of the second computer before transmitting the patient webpage to the second computer, wherein the doctor is not a primary treating doctor for the patient.

16. The method of claim 7, wherein the patient medical records are associated with a medical condition of the patient, and wherein the patient webpage contains links to care protocols for the medical condition.

17. The method of claim 7, further comprising:
receiving, at the server computer system, geolocation data associated with a patient identification object; and
verifying that the patient is in possession of the patient identification object by analyzing the geolocation data associated with the patient identification object, before transmitting the patient webpage to the mobile electronic device.

18. The method of claim 7, further comprising:
in response to the network resource locator being accessed, automatically generating a notification message to a primary care physician of the patient, indicative that the network resource locator has been accessed.

19. A server computer system comprising:
a processor and a memory accessible to the processor; and
a patient data module executable by the processor to cause the server computer system to:
 access patient medical records pertaining to a patient;
 process the patient medical records to extract patient medical data pertaining to the patient and to create a single database record for the patient, the single database record containing the patient medical data pertaining to the patient;
 create a patient webpage specific to the patient from the single database record for the patient, the patient webpage including the patient medical data;
 store the patient webpage;
 receiving a code at the server computer system from a user device that is remote from the server computer system, the code having been displayed, prior to said receiving the code, by a display device included in a patient identification object that has a physical form that enables the patient identification object to be carried on the body or in clothing or a personal accessory of a person, the patient identification object further including a processor an embedded fingerprint scanner, the code further having been displayed by the display device in the patient identification object in response to the processor in the patient identification object determining that a fingerprint acquired by the embedded fingerprint scanner matches a stored fingerprint;
 determining, by the server computer system, whether the code is correct;
 in the event that the personal identifier is determined to be correct, transmitting, by the server computer system, the patient webpage to the second computer in response to a request in connection with the patient being treated by or seeking treatment or advice from a first health care provider other than a primary care physician of the patient; and
 in response to an accessing of a network resource locator corresponding to the patient webpage, automatically generating a notification message to a primary care physician of the patient, indicative that the network resource locator has been accessed, wherein the patient webpage is not owned or controlled by the first health care provider or the primary care physician of the patient.

* * * * *